United States Patent [19]
Huebner

[11] Patent Number: 5,944,721
[45] Date of Patent: Aug. 31, 1999

[54] METHOD FOR REPAIRING FRACTURED BONE

[76] Inventor: Randall J. Huebner, 18650 SW. Hart Rd., Aloha, Oreg. 97005

[21] Appl. No.: 08/986,717

[22] Filed: Dec. 8, 1997

[51] Int. Cl.$^6$ ................................................ A61B 17/56
[52] U.S. Cl. .......................... 606/73; 606/76; 606/77; 606/70; 606/71; 606/69; 606/73; 606/72; 623/16
[58] Field of Search ................. 606/76, 77, 70, 606/71, 69, 73, 72; 623/16

[56] References Cited

U.S. PATENT DOCUMENTS

| | | |
|---|---|---|
| 2,621,145 | 12/1952 | Sano . |
| 4,356,572 | 11/1982 | Guillemin et al. . |
| 4,394,370 | 7/1983 | Jefferies . |
| 4,440,750 | 4/1984 | Glowacki et al. . |
| 4,550,449 | 11/1985 | Tunc . |
| 4,637,931 | 1/1987 | Schmitz . |
| 4,781,813 | 11/1988 | Archer et al. . |
| 4,846,838 | 7/1989 | Takai et al. . |
| 4,880,610 | 11/1989 | Constantz . |
| 4,882,149 | 11/1989 | Spector . |
| 4,898,186 | 2/1990 | Ikada et al. . |
| 5,061,286 | 10/1991 | Lyle . |
| 5,067,963 | 11/1991 | Khouri et al. . |
| 5,073,373 | 12/1991 | O'Leary et al. . |
| 5,108,399 | 4/1992 | Eitenmuller et al. . |
| 5,169,400 | 12/1992 | Mühling et al. . |
| 5,236,457 | 8/1993 | Devanathan . |
| 5,284,655 | 2/1994 | Bogdansky et al. . |
| 5,290,558 | 3/1994 | O'Leary et al. . |
| 5,356,629 | 10/1994 | Sander et al. . |
| 5,397,572 | 3/1995 | Coombes et al. . |
| 5,470,334 | 11/1995 | Ross et al. . |
| 5,584,836 | 12/1996 | Ballintyn et al. . |

FOREIGN PATENT DOCUMENTS 0 011 528 A1  5/1980  European Pat. Off. .

OTHER PUBLICATIONS

"Refractures After Forearm Plate Removal," Rumball et al., *Journal of Orthopaedic Trauma*, vol. 4, No. 2, pp. 124–129, 1990.

*Primary Examiner*—Michael Buiz
*Assistant Examiner*—(Jackie) Tan-Uyen T. Ho
*Attorney, Agent, or Firm*—Kolisch, Hartwell, Dickinson, McCormack & Heuser

[57] ABSTRACT

A method for repairing fractured bone. The method includes the steps of reducing the fracture, securing a fixation device to the bone through at least one hole formed in the bone in order to stabilize the fracture, removing the fixation device from said bone after the fracture has healed, providing an osteoductive resorbable bone implant, and inserting the resorbable bone implant into the hole in the bone so that bone growth into the hole is facilitated.

9 Claims, 2 Drawing Sheets

METHOD FOR REPAIRING FRACTURED BONE

FIELD OF THE INVENTION

The present invention relates generally to a method for repairing a fractured bone. More specifically, the invention concerns a method for eliminating residual holes after treatment of a fracture with a fixation device held in place by attachment through holes in the bone.

BACKGROUND OF THE INVENTION

In treating bone fractures, it is sometimes necessary to stabilize the fracture with a fixation device during healing. Probably the most common device used for internal stabilization of fractures is a rigid metal plate which is placed on the bone spanning the fracture. The plate is held in place by one or more screws on each side of the fracture. The plate and screws reinforce the bone and keep it alignment during healing.

Bone plates and other internal fixation devices may either be left in place after healing or removed. Leaving the plate and screws in situ exposes the patient to the risk that this hardware will interfere with the natural physiology of the bone. In particular, the bone may weaken as it unnaturally relies on the plate and screws for support. On the other hand, removing the plate and screws requires a separate operation with the attendant risks and leaves residual holes in the bone. These residual holes weaken the bone such that the bone is subject to refracturing at the site of a hole and they close very slowly, if ever, on their own.

Fracture of the bone at or near the location of a previous fracture, as at a residual hole, causes a patient great pain and discomfort, and complicates the healing process. After a refracture, it is often difficult to site necessary fixation devices because adequate locations may intersect residual holes left from previous devices. Further, a refracture often leaves the bone weaker than it was following the initial fracture, and consequently requires more time to heal.

One way of eliminating the need for a subsequent operation to remove a fixation device involves the use of resorbable or bioabsorbable fixation devices. U.S. Pat. No. 4,550,449 discloses a bone fixation device fabricated entirely from resorbable materials. Resorbable devices are less likely to leave residual holes because the bone around a hole is free to grow into the hole as the device is resorbed into the body. In addition, a resorbable fixation device left in situ does not pose the risk of interference with the natural physiology of the bone created by a metal device because the resorbable device eventually is absorbed into the body and ceases to provide support to the bone. However, resorbable devices are not as strong as metal devices and do not provide sufficient support for many patients. In these patients, metal fixation devices are preferable, despite the risks associated with either leaving the devices in situ or removing them after the fracture has mended.

It is therefore an object of the present invention to eliminate residual holes resulting from treatment of a fracture with a fixation device secured to the bone by attachment through holes in the bone.

It is a further object of the present invention to provide a method for the repair of a bone fracture using a metal or other nonresorbable fixation device which eliminates bone atrophy caused by leaving the device in situ, while decreasing the risk of refracture at the site of residual holes left after the device is removed.

SUMMARY OF THE INVENTION

The present invention is a method for repairing a fractured bone including the steps of reducing the fracture, securing a fixation device to the bone through at least one hole formed in the bone in order to stabilize the fracture, removing the fixation device from said bone after the fracture has healed, providing an osteoductive resorbable bone implant, and inserting the resorbable bone implant into the hole in the bone so that bone growth into the hole is facilitated.

These and other objects and advantages of the invention will be more fully understood by reference to the accompanying drawings and the following detailed description.

DETAILED DESCRIPTION OF THE PREFERRED EMBODIMENT

Figure 1:
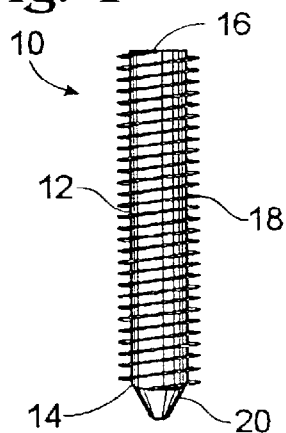
FIG. 1 is a side view of a preferred embodiment of a resorbable bone implant utilized in the present invention.
Figure 2:
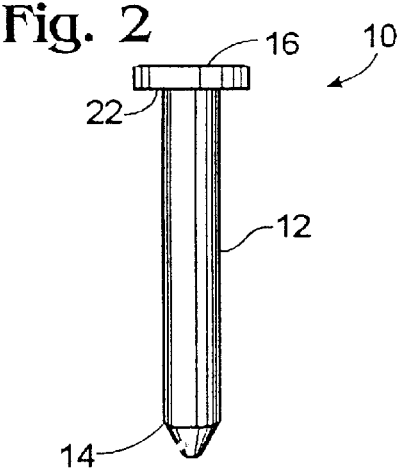
FIG. 2 is a side view of another embodiment of the resorbable bone implant.

FIG. 1 depicts a preferred embodiment of a resorbable bone implant 10 designed for insertion into a residual hole left after removal of a fixation device from a bone. Resorbable bone implant 10 includes a shaft 12 with a leading end 14 and a trailing end 16. The resorbable bone implant includes a textured region at least partially along the length of shaft 12. Preferably, the textured region is formed by threads 18. The leading end 14 has a tapered section 20 for easy insertion. In another embodiment of the resorbable bone implant, shown in FIG. 2, trailing end 16 terminates in a cap 22. Shaft 12 of other embodiments of the present invention may be wholly or partially smooth or textured, or a combination thereof, to provide an effective mating surface.

Figure 3:
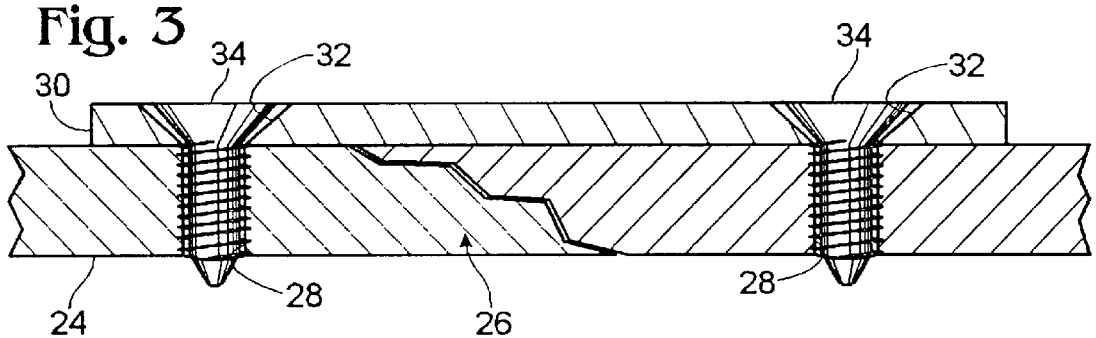
FIG. 3 is a cross-sectional view of a metal plate attached by screws to a fractured bone.

FIGS. 3–6 depict the method of the present invention for treating a bone fracture. As shown in FIG. 3, a bone 24, having a fractured region 26, is treated by drilling holes 28 in bone 24 on either side of fractured region 26. Preferably, holes 28 in bone 24 are drilled using a plate 30 as a guide, such that plate 30 is positioned across fractured region 26 and holes 28 are drilled in bone 24 through pre-drilled holes 32 in plate 30, after reduction of the fracture.

Preferably, the diameter of each of the holes in the plate is slightly larger than the diameter of the corresponding holes in the bone. Screws 34 are provided and are dimensioned so that the outside thread diameter is slightly smaller than the inside diameter of corresponding hole 32 in plate 30 and slightly larger than the inside diameter of corresponding hole 28 in bone 24. Plate 30 is secured to bone 24 by passing each of screws 34 through a corresponding hole in the plate and screwing each of said screws into the corresponding hole in the bone.

Once the plate is secured, it supports and reinforces bone 24 to allow the natural physiological mechanisms of the body to heal fractured region 26 in bone 24. After the bone is sufficiently healed, plate 30 and screws 34 are removed from bone 24 in a subsequent operation.

Figure 4:
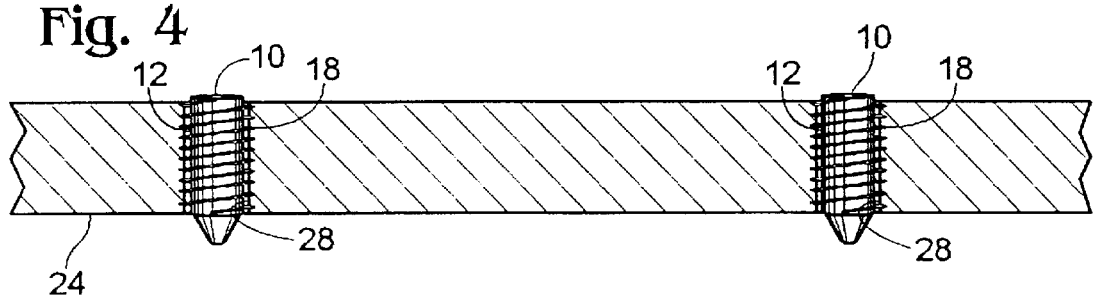
FIG. 4 is a cross-sectional view of a bone having resorbable bone implants inserted into holes in the bone.

As shown in FIG. 4, after removal of plate 30 and screws 34, resorbable bone implants 10 are provided and inserted into holes 28 in bone 24. In a preferred embodiment, resorbable bone implants 10 are threaded and have an outside thread diameter slightly larger than the inside diameter of corresponding hole 28, so that resorbable bone implant 10 may be held in hole 28 by threads 18 screwing into bone 24. Alternatively, resorbable bone implants 10 have an outside diameter slightly smaller than the inside diameter of holes 28, and are held in hole 28 by tissues surrounding hole 28. In yet another embodiment, resorbable bone implants 10 have a smooth shaft and are held in hole 28 by an interference fit between the shaft and the bone. Shaft 12 may also be wholly or partially textured to grip bone 24.

Figure 5:
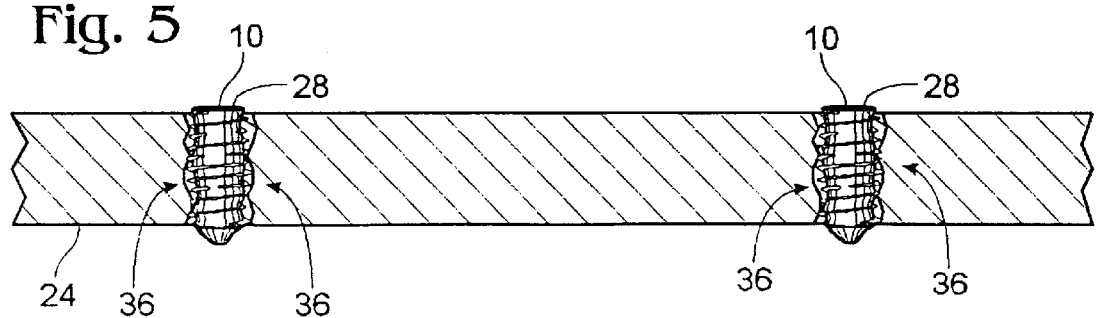
FIG. 5 is a cross-sectional view of a bone after the resorbable bone implants have partially resorbed and the bone has partially grown into the area of the holes.
Figure 6:
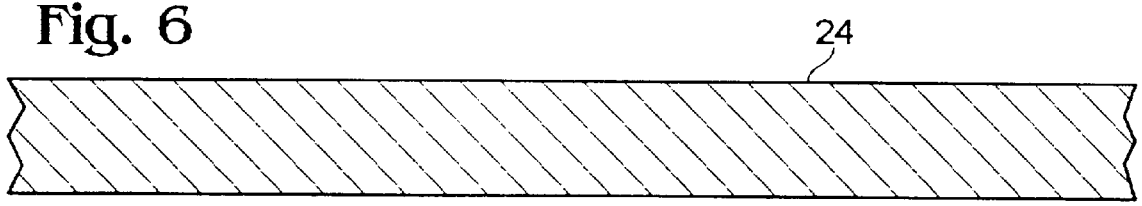
FIG. 6 is a cross-sectional view of a bone after the resorbable bone implants have fully resorbed and the bone has fully grown into the area of the holes.

As shown in FIG. 5, some time after resorbable bone implants 10 are inserted into holes 28, the body begins to resorb the resorbable bone implants 10, and the resorbable bone implants 10 shrink in size. Resorbable bone implants 10 contain osteoductive nutrients that aid and/or stimulate bone growth, so as implants 10 are resorbed nutrients are released to the bone, and bone growth is facilitated in regions 36 of bone 24 adjacent to implant 10. Bone growth in regions 36 strengthens the bone and reduces the risk of refracture in the area of hole 28. Preferably, bone growth continues until the hole is completely closed and bone 24 is a seamless section of bone, as shown in FIG. 6. Although in some cases the hole may not be able to close fully, even partial growth of the bone into the hole strengthens the bone and reduces the risk of refracture.

Although FIGS. 3–6 depict the present invention being employed with an internal fixation device in the form of a plate and screws, the present invention may be practiced on a bone fracture repaired with any type of fixation device which penetrates the bone and leaves residual holes in the bone when removed. For example, the present invention may be used in conjunction with other types of internal fixation devices, as well as to fill holes left from mounting hardware of external fixation devices.

Figure 7A:
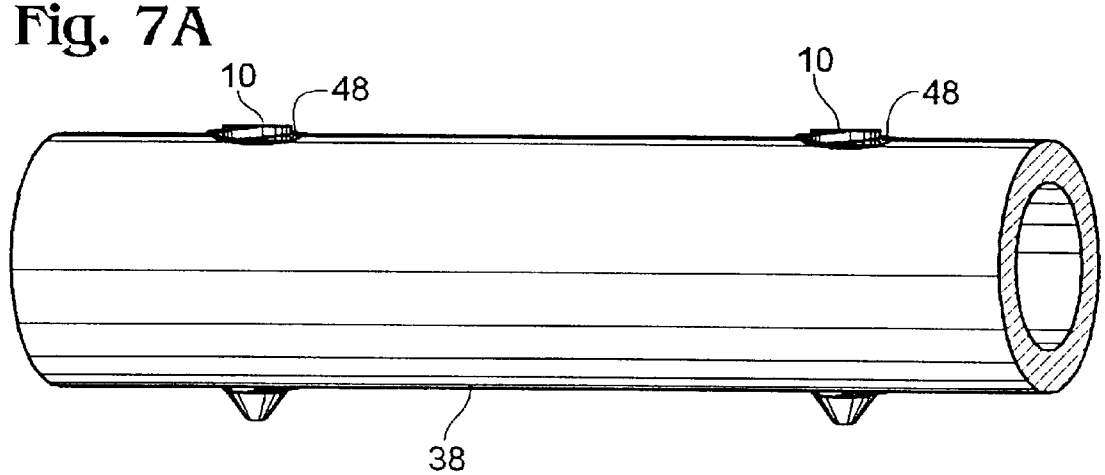
FIG. 7A is a side view of a hollow bone after resorbable bone implants have been inserted into a residual hole in the bone, spanning the medullar canal.
Figure 7B:
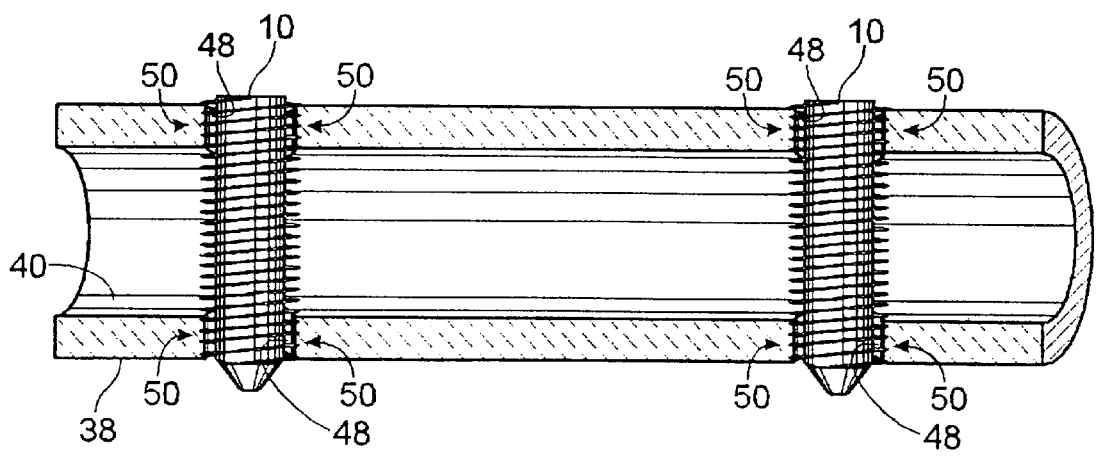
FIG. 7B is a cross-sectional view of a hollow bone after resorbable bone implants have been inserted into a residual hole in the bone, spanning the medullar canal.

As shown in FIGS. 7A and 7B, resorbable bone implants 10 can also be used in a hollow bone 38 having a medullar canal 40. After aligning and reinforcing the hollow bone 38 with a fixation device, allowing a fracture in the bone time to heal, and removing the fixation device in a subsequent operation, resorbable bone implants 10 are inserted into residual holes 48, spanning medullar canal 40. Thus, the implant can be used to treat holes which pass through both sides of the bone. As previously described, osteoductive nutrients in resorbable bone implants 10 are released over time and facilitate bone growth in regions 50 adjacent to residual holes 48.

I claim:

1. A method for repairing a fractured bone, comprising the steps of:

reducing the fracture;

securing a fixation device to the bone to stabilize the fracture, where the fixation device is secured to the bone through at least one hole formed in the bone;

removing the fixation device from said bone after the fracture has healed;

providing an osteoductive resorbable bone implant; and inserting the osteoductive resorbable bone implant into the hole in the bone after the step of removing so that bone growth into the hole is facilitated.

2. The method of claim 1, further including the step of choosing a plate for the fixation device, wherein the plate includes plural holes.

3. The method of claim 1, further including the step of positioning the osteoductive resorbable bone implant to span a medullar canal within the bone.

4. The method of claim 1, further including the step of choosing the osteoductive resorbable bone implant to include a shaft having a leading end and a trailing end.

5. The method of claim 4, further including the step of selecting the osteoductive resorbable bone implant to include a textured region at least partially along the shaft, the textured region being configured to engage the bone.

6. The method of claim 5, further including the step of selecting the textured region to include threads configured to engage the bone.

7. The method of claim 4, further including the step of choosing the shaft to include a smooth surface.

8. The method of claim 4, further including the step of choosing the osteoductive resorbable bone implant to include a cap attached at the trailing end of the shaft, the cap being configured to prevent the trailing end from entering the hole in the bone.

9. The method of claim 1, wherein the bone includes a medullary canal and the hole passes through the bone on both sides of the medullary canal and wherein, in the step of inserting, the osteoductive resorbable bone implant is positioned to fill the hole on both sides of the medullary canal.

* * * * *